United States Patent

Coucher

[11] 3,938,525
[45] Feb. 17, 1976

[54] PLASMA SURGERY
[75] Inventor: Robert G. Coucher, Salt Lake City, Utah
[73] Assignee: Hogle-Kearns International, Salt Lake City, Utah
[22] Filed: May 15, 1972
[21] Appl. No.: 253,494

[52] U.S. Cl. ............................................. 128/303.1
[51] Int. Cl.² ............................................ A61N 1/44
[58] Field of Search....... 128/303.1, 303.14, 303.17; 204/164, 312; 315/111; 313/231; 317/4; 219/121 P

[56] References Cited
UNITED STATES PATENTS

| | | | |
|---|---|---|---|
| 3,424,661 | 1/1969 | Androshuk et al. | 204/164 |
| 3,434,476 | 3/1969 | Shaw et al. | 128/303.1 |
| 3,444,061 | 5/1969 | Hellund | 204/164 |
| 3,585,441 | 6/1971 | LaRocca | 313/231 |

Primary Examiner—William E. Kamm
Attorney, Agent, or Firm—Trask & Britt

[57] ABSTRACT

An electrically neutral, D.C.-induced cold plasma is used to cauterize tissue in the vicinity of a surgical incision. The incision may itself be formed by such a plasma.

6 Claims, 3 Drawing Figures

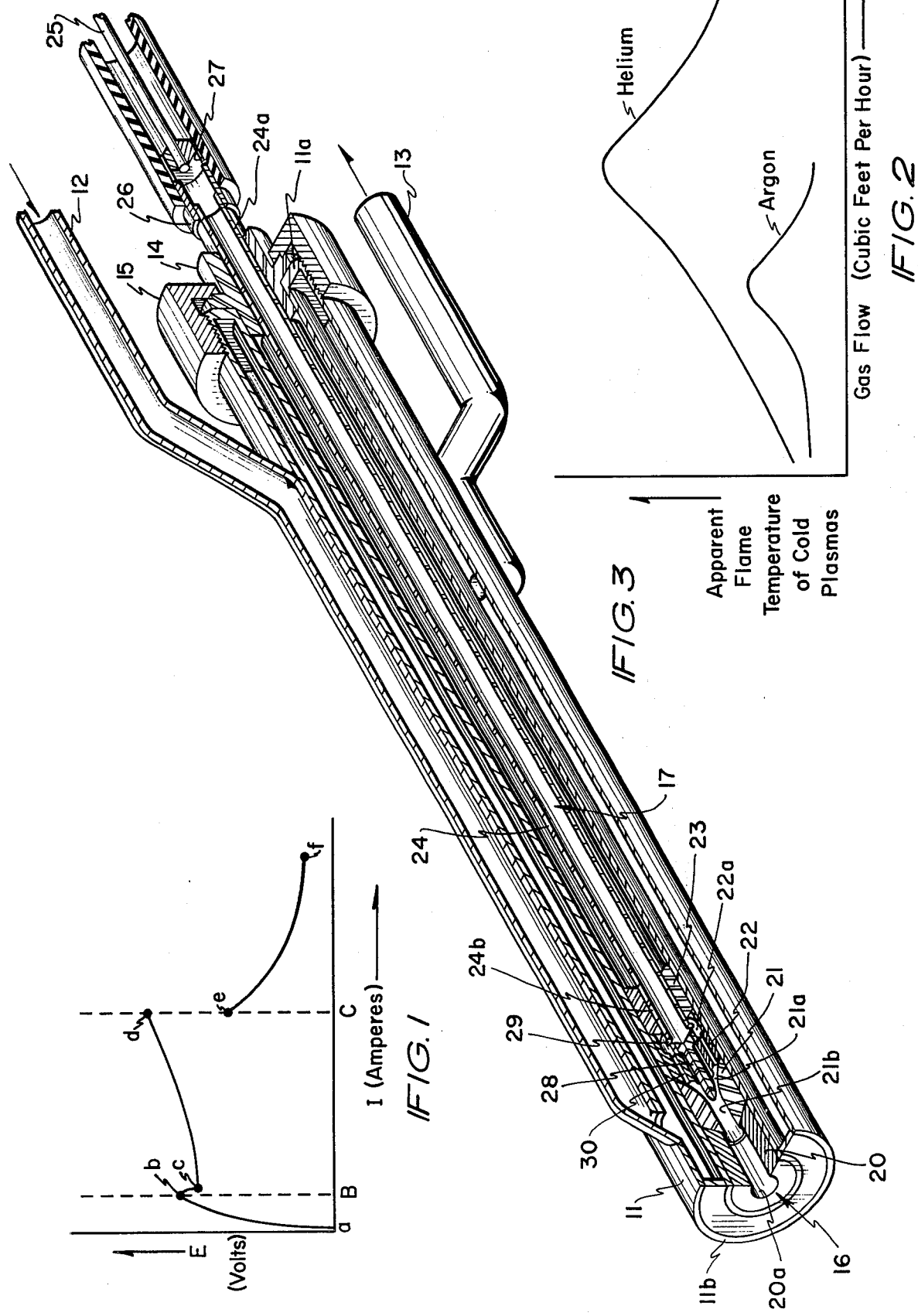

PLASMA SURGERY

RELATED APPLICATIONS

Commonly assigned, copending application Ser. No. 79,840, filed Oct. 12, 1970, now U.S. Pat. No. 3,903,891, discloses and claims methods and apparatus for plasma surgery. According to that application, a cold plasma is established and attenuated to a small cross section. This plasma is applied to tissue to produce an incision. The present application claims the additional discovery that an electrically neutral, D.C.-induced cold plasma is especially useful for surgical applications.

BACKGROUND OF THE INVENTION

Field

This invention relates to surgery, specifically that involving the application of plasma to tissue.

State of the Art

"Glow discharge" phenomena are well known. The most familiar applications of such phenomena are in lighting, e.g., in fluorescent, neon, sodium and mercury lamps. Glow discharge plasmas are often described as "cold plasmas" because the energy density and wall-heating effect of such plasmas are very low. Such plasmas may also be regarded as being at thermal nonequilibrium because their gas temperatures are characteristically much lower than their "electron temperatures." The term "electron temperature" denotes a temperature (usually several thousand degrees) corresponding to the energy possessed by the electrons in a plasma. It is commonly understood that the operating conditions productive of cold plasmas are high voltage (1 – 100kV) and low pressure (usually below 10 torr). The term "cold plasma," as used in the following specification and claims, is intended to include plasmas at thermal nonequilibrium which evidence a low wall-heating effect, whether or not such plasmas exhibit the appearance and other physical characteristics normally associated with the specific cold plasma and glow discharge phenomena heretofore recognized in the art. According to this invention, cold plasmas may be produced which possess a very high energy density, for example.

As used in this specification and in the appended claims, the term "plasma" is used in its broadest context and refers to an at least partially ionized gas, which may include molecules, atoms, ions, electrons and free radicals, each moving with a velocity dependent upon its mass and its temperature. (A plasma is regarded as at thermal equilibrium only when the distribution of its particle velocities is such that the average energy of each species is approximately the same.) The average energy of a particle (e.g., an electron) can be expressed as a temperature (e.g., "electron temperature") according to the relationship $$\frac{1}{2} mV^2 = \frac{3}{2} kT,$$

where $m$ is the mass of the particle, $V$ is the root-mean-square velocity of the particle, $k$ is Boltzmann's constant, and $T$ is the absolute temperature of the particle. The term "plasma" includes gases ionized to a very limited extent, e.g., 0.1 percent of its molecules, although it is often preferred to refer to such gases as being in an "energized" state. The term "energized" gas refers to any gas, whether ionized or not, which is storing energy, as a result of the application of electrical energy, in a form capable of subsequent release as heat and/or light. This term thus includes a gas which is ionized, disassociated, or in an "excited" state, including the "metastable" state. A gas is considered to be in an "excited" state when an electron of an inner orbital shell of a species (molecules, atoms, and/or ions) has absorbed a quantum of energy so that it is at a higher-than-its-ground-state energy level with respect to the nucleus; it is considered to be in the "metastable" state when an inner electron is excited to a level from which the return to ground via electro-magnetic emission is of extremely low probability. A species in the metastable state generally loses its excess energy either by imparting kinetic energy to its surroundings or by exciting other molecules, atoms or ions.

The use of D.C. arc plasma for surgery is suggested by U.S. Pat. No. 3,434,476, which discloses and claims apparatus intended for use as a surgical scalpel. The apparatus thus disclosed is apparently incapable of producing plasmas which are not substantially at thermal equilibrium. This instrument is reported to be unsafe for actual clinical use because it tends to char tissue. It is recognized in the disclosure of the aforementioned application Ser. No. 79,840 that plasmas of metastable noble gas are preferred for surgical applications. Heretofore, the advantages of electrically neutral, D.C.-induced cold plasmas for this purpose have not been suggested, however.

SUMMARY OF THE INVENTION

It has been found that many of the problems associated with plasma surgical techniques are obviated by the use of electrically neutral, D.C.-induced cold plasma. Such plasmas have sufficient energy to produce surgical incisions within tolerable time limits, but avoid the problems characteristic of hot plasma surgery. An important characteristic of the electrically neutral, D.C.-induced cold plasmas of this invention is their remarkable efficacy for cauterizing tissue in the vicinity of a surgical incision. This characteristic is extremely useful, enabling a surgeon to prepare a clean and sterile incision, free from interfering body fluids. Accordingly, the surgical techniques of this invention include embodiments in which the plasma is used solely for its cauterizing properties, as well as embodiments in which the plasma is relied upon both for producing a surgical incision and for cauterizing tissue in the region of the incision.

Although it is possible to produce an electrically neutral, rf-induced plasma, it is inefficient to do so. Moreover, rf plasma devices are less stable and impose far greater risks of accidental electrocution. Hot D.C. plasmas are of only minor utility for surgical applications because of the disadvantages referred to hereinbefore. The electrically neutral, D.C.-induced cold plasmas of this invention are highly stable and controllable. The characteristics of the plasma are variable over a wide, useful range by adjusting simple parameters, such as orifice diameter, orifice material, gas species, flow rate and power settings.

BRIEF DESCRIPTION OF THE DRAWINGS

In the drawings, which illustrate what is presently regarded as the best mode for carrying out the invention:

FIG. 1 is a graph showing a typical plot of voltage versus current and illustrates the manner in which power settings may be used to control plasma characteristics;

FIG. 2 is a graph showing typical plots of apparent flame temperature versus gas flow and illustrates how selection of carrier gas and flow rates influences plasma characteristics; and FIG. 3 is a pictorial view, partially in section, of a D.C. plasma scalpel useful for the practice of this invention.

DESCRIPTION OF THE PREFERRED EMBODIMENTS

The surgical methods of this invention utilize plasmas represented by line $c$-$d$ of FIG. 1. Although the exact voltage and current values represented by the curve will depend upon the particular gas being excited, the plot of FIG. 1 is generally illustrative of the behavior of any gas which might be used for plasma surgical applications.

When a potential is applied by a power source to a gas, e.g., Argon or Helium, the gas will carry very little current until the potential exceeds its ionization potential, designated $b$ in FIG. 1. The gas will then ignite, and it will assume plasma characteristics dependent upon the current available to it from the power source. As can be seen from the drawing, increasing the power applied to the gas will result in very small increases in the voltage drop across the plasma but correspondingly large increases in the current carried by the plasma. The power settings are thus controlled to maintain current between the levels indicated B and D, respectively. Operation on the region $b$-$c$ of the curve is less stable, so the power is desirably held sufficiently high to avoid operating in this region. If the current exceeds the level indicated D, the plasma assumes the characteristics of a hot plasma (region $e$-$f$ of the curve).

Once it is recognized that the "cold plasma" region is preferred for surgery, an operator will have no difficulty in determining proper power settings for any surgical plasma gas. FIG. 1 also shows that a surgeon can control the amount of energy applied to tissue by increasing the power applied to the gas, provided the power level is held below the critical "arcing" level (point d) of the particular gas.

The temperature of the plasma may be controlled to a considerable degree, as illustrated by FIG. 2, by proper selection of the plasma gas and by adjusting the flow rate of the gas. As illustrated by FIG. 2, a cold Helium plasma will generally exhibit a much higher apparent temperature than will a cold Argon plasma. In either case, maximum cutting ability will correspond to the region of highest apparent temperature, which region will correspond to a relatively narrow range of gas flow rates. Similar curves can be easily developed for any desired surgical plasma gas. FIG. 2 illustrates the ease with which a surgeon can control the temperature of the plasma flame through the simple expedient of adjusting the gas flow rate. Moreover, substantially similar plasma flame temperatures are available at two different flow rates. A surgeon thus has the opportunity to select which flow rate he desires for a particular purpose. "Apparent temperature" is plotted on FIG. 2 because the data for the plots was obtained by thermocouple measurements. Because of the size of the thermocouple with respect to the plasma column, the thermocouple effect cannot reflect true temperatures, but only relative temperatures.

Other adjustments may be provided in the surgical handpiece, as illustrated by FIG. 3. The apparatus there shown comprises a generally cylindrical annular case 11 in open communication with an inlet 12 and outlet 13, respectively, for a cooling fluid, typically water. One end 11$a$ of the case is sealed with an insulator 14 held in place by a cap 15 as shown. The opposite end 11$b$ of the case contains a nozzle assembly, indicated generally 16. An anode assembly, indicated generally 17, extends through the insulator 14 and terminates within the nozzle assembly 16 as shown.

Coolant is introduced into inlet 12 and contacts the internal structure encasing the anode assembly 16. It then flows back through annular case 11 and exits from the outlet 13.

The nozzle assembly 16 includes a cathode 20 at its extreme end, a constrictor section 21, a gas entry section 22 and an anode entry section 23. These components are machined from nonconductive material, e.g., boron nitride, except for the cathode, which is of a selected conductive material. The anode assembly 17 includes a hollow conductive tube 24 connected to a power supply by a conductor 25. The tube 24 is sealed at the cap end 24$a$ to an anode connector 26. This connector has gas entry ports 27 which openly communicate with the interior of the tube 24. An anode 28 is conductively connected to one end 24$b$ of the tube 24 which is sealed into the anode entry section 23 of the nozzle assembly 16 and terminates in the gas entry chamber 22$a$ of the gas entry section 22. The wire anode 28 is thus centrally disposed in the nozzle entry chamber 21$a$ of the constrictor section 21.

D.C. power and gas are both introduced to the handpiece through the connector 26. Gas enters the holes 27, flows down the tube 24 out gas exit ports 29 into the chamber 22$a$, from which it flows through channels 30 into the nozzle entry chamber 21$a$ adjacent the anode 28. The potential difference between the cathode 20 and the anode 28 ignites the gas to a plasma flame. The flame is attenuated by the nozzle throat portion 21$b$ of the constrictor section 21 and exits through the orifice 20$a$ of the cathode 20 (the nozzle exit) as an electrically neutral cold plasma, assuming that appropriate power settings are maintained as previously described.

Two useful control variables are available within the nozzle assembly. These are the orifice diameter of the nozzle and the material of construction of the cathode. Nozzle diameter influences the back pressure in the handpiece, resulting in a change in potential drop at the cathode. It has been found that increasing the orifice diameter by about fifty percent, from about 0.02 to about 0.03 inches, shifts the position of the line $c$-$d$ of FIG. 1 up almost 100 volts. In practice, orifice diameters of between about 0.005 to about 0.05 inches have been found to be useful in surgical handpieces according to this invention. The power available in the handpiece from a fixed power source may be adjusted by changing the composition of the cathode. For example, approximately 50 percent more power is available using a tungsten cathode than is available when a copper cathode is used, corresponding to a 50 percent increase in the median glow region voltage.

In practice, a surgeon may prefer certain combinations of gas species, flow rate, orifice diameter, power settings and cathode composition based upon his own experience and the specific objective of the operation. In general, however, virtually any D.C.-induced, electrically neutral, cold plasma has utility for surgical applications, especially if the plasma is attenuated to sufficiently small cross section to permit a narrow region of contact between the plasma and the tissue being treated. The preferred plasma column diameter at present is between about 0.005 and 0.05 inches, corresponding to orifice diameters of approximately that size. Nichrome wire suffices as an anode material, whereas the cathode may be either copper, tungsten or other conductive material. Suitable surgical gases include Argon, Helium and sometimes Nitrogen, usually in admixture with one of the noble gases.

Reference herein to details of the preferred and illustrated embodiments is not intended to restrict the scope of the appended claims, which themselves recite those details regarded as essential to the invention.

As used herein, the term "ignite" should be understood to refer to the transformation of a gas to the plasma state under the influence of an electric field. This phenomenon is of course dissimilar from combustion.

I claim:

1. A method for cauterizing tissue adjacent a surgical incision, which comprises:

establishing and maintaining an electrically neutral, D.C.-induced cold plasma of sufficiently small cross section to permit a narrow region of contact between the plasma and tissue; and applying the plasma to tissue adjacent a surgical incision to cauterize the same.

2. A method according to claim 1, wherein the plasma is applied to tissue to both produce an incision and to cauterize the tissue adjacent the incision so produced.

3. A method according to claim 1, wherein the plasma is established and maintained by applying D.C. power to a gas selected from the group consisting of Argon, Helium, Nitrogen and mixtures of two or more thereof.

4. A method according to claim 1, wherein the diameter of the plasma is held to between about 0.005 and about 0.05 inches.

5. In the method of performing surgery by contacting tissue with a plasma to form an incision, the improvement which comprises using an electrically neutral, D.C.-induced cold plasma to cauterize tissue in the region of the incision.

6. The improvement of claim 5, wherein said electrically neutral, D.C.-induced cold plasma is also used to form said incision.

* * * * *